United States Patent [19]

Katopodis

[11] Patent Number: 4,748,128

[45] Date of Patent: May 31, 1988

[54] METHOD FOR DETERMINING LIPID BOUND SIALIC ACID IN PLASMA

[75] Inventor: Nonda Katopodis, Stamford, Conn.

[73] Assignee: Dianon Systems, Inc., Stratford, Conn.

[21] Appl. No.: 711,591

[22] Filed: Mar. 18, 1985

Related U.S. Application Data

[63] Continuation-in-part of Ser. No. 595,310, Mar. 30, 1984, abandoned.

[51] Int. Cl.[4] .................. G01N 33/00; G01N 33/48; G01N 31/22; G01N 1/18

[52] U.S. Cl. .................................. 436/93; 422/61; 436/64; 436/71; 436/87; 436/164; 436/178

[58] Field of Search .............. 436/64, 129, 813, 63, 436/71, 87, 93, 94, 164, 177, 178; 530/420; 422/61

[56] References Cited

U.S. PATENT DOCUMENTS

| | | | |
|---|---|---|---|
| 4,115,062 | 9/1978 | Morre et al. | 424/12 |
| 4,146,603 | 3/1979 | Davidson et al. | 436/540 X |
| 4,342,567 | 8/1982 | Katopodis et al. | 436/64 |
| 4,457,865 | 7/1984 | Miller | 436/813 X |
| 4,493,898 | 1/1985 | Sallay | 436/64 |

OTHER PUBLICATIONS

Silver et al., Cancer Research, 39: 5036–5042, 1979.
Kloppel et al., Proc. Nat'l. Acad. Sci., USA, vol. 74, No. 7, pp. 3011–3013, Jul. 1977.

*Primary Examiner*—Robert J. Warden
*Assistant Examiner*—Shawn P. Foley
*Attorney, Agent, or Firm*—John P. White

[57] ABSTRACT

The amount of lipid bound sialic acid in a blood plasma or serum sample may be determined by a method which may be automated involving the following steps: diluting the sample with distilled water; mixing and then cooling the diluted sample; adding a mixture of a chlorinated lower alkyl hydrocarbon and a lower alkyl alcohol; mixing, diluting with water and then treating by mixing further and centrifuging to yield a substantially clear upper phase; recovering the upper phase and adding to it a mixture of a protein precipitating agent and adsorbing material, mixing the resulting admixture; recovering the resulting precipitate, suspending the precipitate in distilled water and determining the amount of lipid bound sialic acid present.

35 Claims, No Drawings

METHOD FOR DETERMINING LIPID BOUND SIALIC ACID IN PLASMA

BACKGROUND OF THE INVENTION

This application is a continuation-in-part of U.S. Ser. No. 595,310, filed Mar. 30, 1984, now abandoned the contents of which are hereby incorporated by reference into the present application.

This invention concerns an improved method for the determination of lipid bound sialic acid in plasma or serum which is less time-consuming, less expensive, less variable from sample to sample and less dependent upon the skill and experience of the person performing the test.

Much work has been done which indicates that elevated sialic acid content in blood sera of a patient is an indication of the presence of cancer.

Thus, for example, U.S. Pat. No. 4,146,603 to Davidson et al. discloses and claims a fairly complex series of procedures whereby elevated sialic acid content is a determinant with respect to cancer specific determinations.

MacBeth and Bekesi, Cancer Res. 22: 1170-1176 (1962) measured plasma glycoproteins and found galactose and mannose values were seen in breast cases without metastases. Kloppel et al., Proc. Natl. Acad. Sc. 74: 3011-3013 (1977) reported 2.5-fold increases of serum sialic acid glycolipids in mice bearing transplantable mammary carcinomas and 2-fold increases in human carcinoma patients. The method involved column chromatographic separation of the gangliosides. A minimum of 1 ml whole blood was required. Kloppel et al., Am. J. Vet. Res. 39: 1377-1380 (1978) also reported increases of sialic acid in 92% of 24 dogs; however, a number of false positives were observed in dogs with other disorders. In leukemic AKR/J mice, Lengle, J. Natl. Cancer Inst. 62: 1565-1567 (1979) found increased lipid bound sialic acid in their plasma and thymic lymphocytes. Lipid bound sialic acid levels were found increased in plasma and erythrocytes of humans bearing melanomas. Portoukalian et al., Biochem. Biophys. Res. Commun. 85: 916-920 (1978). Chromatographic separation and purification on columns was followed by evaluation on chromatoplates. Silver et al., Cancer 41: 1497-1499 (1978); Cancer Res. 39: 5036-5042 (1979) have reported elevated serum sialic acid values in melanoma patients that were significantly related to the tumor burden. However, 36% of patients with observable tumors showed no elevated serum sialic acid. Hogan-Ryan et al., Br. J. Cancer 41: 587-592 (1980) reporting on total bound serum sialic acid in patients with breast cancer found elevations that corresponded with tumor stage.

One specific method over which the present invention is an improvement is disclosed in the American Association for Cancer Research Annual Meeting PROCEEDINGS Vol 21, March 1980 as Abstract No. 728 by Katopodis et al. Briefly, this method requires that a 100 µl plasma sample (reduced to 50 µl) be extracted with 6 ml of a chloroform/methanol mixture, (2 to 1, volume to volume). The lipid extract is then partitioned with 0.2 of its volume of water. The aqueous phase is evaporated to dryness and the residue redissolved in water. The lipid bound sialic acid is then purified by trichloroacetic acid-phosphotungstic acid precipitation and, after the removal of the supernatant from the resultant precipitate, the precipitate is determined by the Svennerholm and Miettien method (Svennerholm, Quantitative Estimation of Sialic Acid . . . , Biochem. Biophys. Acta 24, pp. 604-611 (1957). The other specific method over which the present invention is an improvement is disclosed in Katopodis and Stock, U.S. Pat. No. 4,342,567. This method is similar to the foregoing but requires only about 50 µl of sample rather than the 100 µl required by the prior art method. The drying step is eliminated and there is no use of trichloroacetic acid. Phosphotungstic acid is used alone. This prior method consists essentially of the following steps:

1. To a screw cap culture tube, 13X100 mm, add 150λ distilled water with a 500λ Hamilton syringe. To this tube transfer a capillary pipette (Unopette, Becton-Dickinson 5841) with its content of 44.7λ of plasma (or serum). Vortex the contents for 5 seconds. Transfer the tube to crushed ice.

2. Add to the tube 3.0 ml cold (4°-5° C.) 2:1 v/v mixture of chloroform and methanol and vortex the mixture for 30 seconds.

3. To this mixture add 0.5 ml cold distilled water, cap the tube and mix the contents by repeatedly inverting the tube for 30 seconds.

4. After centrifuging the tube 5 minutes at room temperature at 2500 rpm, transfer 1 ml of the upper layer into a culture tube like the one already used.

5. Add 50λ phosphotungstic acid solution (1 g/ml) and after mixing let it stand at room temperature for 5 minutes.

6. Centrifuge for 5 minutes at 2500 rpm and remove the supernatant by suction.

7. Add 1 ml water and vortex until the precipitate is in suspension without gross particles (about 1 minute).

8. Add 1 ml of the resorcinol reagent, mix and place the tube in boiling water for exactly 15 minutes.

9. Immediately after the 15 minutes, transfer the tube to an ice and water bath and leave for 10 minutes.

10. To the ice cold tube add 2 ml butyl acetate-n-butanol 85:15 v/v mixture at room temperature, vortex and centrifuge for 5 minutes at 2500 rpm.

11. Read the extracted blue color at 580 nm and the amount of lipid bound sialic acid (LSA) is determined by use of a standard curve developed from a standard sample of n-acetyl neuraminic acid (NANA) and use of this formula:

$$\text{LSA (mg/100 ml plasma)} = (x \cdot 100{,}000\lambda)/(y \cdot 44.7\lambda \cdot 1000)$$

$x = \gamma$ NANA read from standard curve for the sample
$y = 1$ ml of supernatant ÷ volume of entire supernatant The preceding method suffers a number of disadvantages including the following: the need for a precisely defined 44.7λ starting sample; lipid bound sialic acid is lost during the tube inversion step creating reduced final values; precipitation of the lipid bound sialic acid with phosphotungstic acid is not complete, which is a particular problem when working with samples in which the amount exceeds normal values by only small amounts (e.g., early in cancer development); the rapidity of the test is limited by the 5 minutes waiting time after phosphotungstic acid addition and the cost of the test is not as low as is desirable.

Using the preceding method different laboratories have obtained results which vary widely. Table I sets forth results obtained by others and illustrates the variability obtained when samples from normal subjects were tested.

TABLE I
RESULTS OBTAINED BY DIFFERENT LABORATORIES USING THE METHOD OF U.S. Pat. No. 4,342,567

NORMAL SAMPLES

| RANGE mgs % | MEAN mgs % | UPPER LIMIT mgs % | |
|---|---|---|---|
| 15.0–20.0 | 17.5 | 20.0 | (1) |
| 12.8–16.8 | 14.8 | 16.8 | (2) |
| 11.6–19.7 | 15.7 | 19.7 | (3) |
| 11.6–19.1 | 15.4 | 19.1 | (4) |
| 15.0–25.0 | 20.0 | 25.0 | (5) |
| 11.1–15.7 | 13.4 | 15.7 | (6) |
| 16.4–26.6 | 21.5 | 26.6 | (7) |
| NO INFO | 15.3 | NO INFO | (8) |
| NO INFO | NO INFO | 17.2 | (9) |
| 12.6–17.2 | 14.9 | 17.2 | (10) |
| 11.9–26.2 | 19.1 | 26.2 | (11) |
| 15.5–22.5 | 19.0 | 22.5 | (12) |
| 8.7–18.5 | 13.6 | 18.5 | (13) |
| 10.9–18.9 | 14.9 | 18.9 | (14) |
| 10.0–21.0 | 15.5 | 21.0 | (15) |
| MEAN - 12.3–20.6 | 16.4 | 18.2 | |

(1) KATOPODIS AND STOCK, U.S. Pat. No. 4,342,567
(2) CHEN SHU-PAN et al., J. SHANGHAI MED. VOL. 6, 1983
(3) A.M. DNISTRIAN et al., CLINICAL CHEM. 27(10) 1981
(4) S. KAKARI et al., ANTICANCER RES. 4, Suppl. 1:3–6, 1984
(5) L. SANTAMARIA et al., MED. BIOLOGIE ENVIR. VOL. 12 1984
(6) A.M. DNISTRIAN et al., AACR VOL. 23, 609, 1982
(7) P. KOSMIDIS et al., ASCO, VOL. 2, C-1, 1983
(8) D. MUNJAL et al., FED. PROC., VOL. 42(3), March 1983
(9) K.M. ERBIL et al., CL. CHEM. 29, VOL. 6(194), 1983
(10) CHEN SHU-PAN et al., CHIN. J. OBSTET. & GYN. 18(4):235–38 1983
(11) L. SALVAGNO et al., 13 INTL. CONG. OF CHEMO., 1983 (VIENNA)
(12) L. SALVAGNO et al., I. OF CANCER RESEARCH, 1983
(13) A. K. BHARGAVA et al., ASCO, VOL. 6, No. 2, 1984
(14) S. KAKARI et al., INTL. MEETINGS, SALONICA, GREECE, 1982
(15) T. WUSTROW, GERMAN CANCER CONGRESS, 25/6 GL 1983

SUMMARY OF THE INVENTION

This invention provides a method for determining the amount of lipid bound sialic acid in a sample of human blood plasma or serum involving the following steps:

(a) diluting a predetermined volume of a blood plasma or serum sample with distilled water to a volume about four times that of the predetermined volume;

(b) mixing the diluted sample for a suitable period of time to obtain a substantially homogeneous sample;

(c) cooling the mixed, diluted sample to about 0°–5° C.;

(d) adding to the cooled sample a mixture of a chlorinated lower alkyl hydrocarbon and a lower alkyl alcohol, the volume of the mixture added being about sixty times the predetermined volume of the blood plasma or serum sample, and the volume ratio of chlorinated hydrocarbon to alcohol in the mixture being about 2:1 and its temperature about 0°–5° C.;

(e) mixing the resulting admixture for a suitable period of time to dissolve matter present in the sample in the chlorinated hydrocarbon/alcohol mixture;

(f) diluting the admixture with deionized distilled water at a temperature from about 0°–5° C., the volume added being about ten times the predetermined volume of the blood plasma or serum sample;

(g) treating the diluted admixture for a suitable period of time to permit formation of a substantially clear upper phase;

(h) separately recovering from the clear upper phase so formed a predetermined volume of the upper phase;

(i) adding to the predetermined volume of the upper phase an amount of a mixture of a protein-precipitating agent and an adsorbing material, the amount of mixture being effective to cause precipitation of the lipid bound sialic acid and to adsorb the precipitated lipid bound sialic acid;

(j) mixing the resulting admixture;

(k) separately recovering the resulting adsorbed precipitate;

(l) suspending the precipitate in a suitable volume of distilled water; and (m) determining the amount of lipid bound sialic acid present in the suspended precipitate and thereby the amount present in the blood plasma or serum sample.

The preferred mixture for effecting precipitation of lipid bound sialic acid is one which comprises about 75% by weight phosphotungstic acid and about 25% by weight silica gel.

Desirably, the plasma sample to be tested is adsorbed to and dried on a suitable support, e.g., a filter paper strip or circle onto which the sample has been dried.

This invention also provides a method and kit for diagnosing cancer in a human subject which comprises determining the amount of lipid bound sialic acid in a sample of a subject's blood plasma or serum and comparing the amount so obtained with values obtained for subjects known to have cancer.

Alternatively the method and kit of this invention may be used to regularly determine the amount of lipid bound sialic acid present in a subject's blood plasma or serum and thus monitor the subject for development of cancer by comparing each amount so determined with amounts previously determined for the subject.

In one embodiment this invention provides an improvement in methods for determining the amount of lipid bound sialic acid in a sample of human blood plasma or serum, which methods involve extraction from the sample, followed by precipitation of lipid bound sialic acid from the extract using a protein precipitating agent. This improvement involves the use of an adsorbing material such as a siliceous material in admixture with the protein precipitating agent.

DETAILED DESCRIPTION OF THE INVENTION

The amount of lipid bound sialic acid in a sample of human blood plasma or serum may be determined and the amount so determined used as a diagnostic indicator of cancer. A preliminary step to the method is to obtain a sample to be tested. The sample will typically be recovered from whole blood drawn from a subject and treated using methods described hereinafter to recover the plasma or serum. The plasma or serum may then be employed directly, and may be maintained at a proper storage temperature, e.g. below about 4° C., during transport or storage by packing the sample in an insulated container with dry ice, or more economically, with a commercially available freeze pack. Preferably, however, the sample is placed on a suitable support and dried, and the sample-bearing support employed in the test by first redissolving the dried sample at the beginning of the assay described hereinafter. Suitable support materials include any adsorbent, bibulous or porous material on which the sample can spread and dry, and which does not interfere with the assay. Numerous suitable support materials known in the blood assay art may be used, e.g. natural or synthetic cellulosic materials such as paper or nitrocellulose in a variety of forms such as a paper strip or circle of compressed cellulosic material. Numerous types of paper strips or circles may be utilized such as filter paper, chromatography paper or specimen collection paper. Examples of such include Whatman Grade 54 and #903 ™ available from Schleicher & Schuell, Keene, N.H. Also suitable are fibrous materials such as glass, natural cloth, e.g. cotton, and synthetic materials such as teflon, nylon and polyolefins, e.g. polyethylene and polypropylene. In the case of glass or synthetic materials, non-fibrous fabricated forms may also be used such as scintered, fritted or otherwise porous strips, circles, etc. Samples may be dried on the inner surface of a test tube or other suitable sample container. Additionally, suitable support materials may also be used in the form of an adsorbent powder packaged in a vial or tube. The use of plasma or serum samples dried on such supports provides major advantages over plasma per se in terms of sample stability, transportation and storage and makes it possible to perform the method of the present invention on samples drawn from patients located at great distances from the actual testing site. Samples prepared on such support materials may be maintained at room temperature for up to one week, e.g. during shipping or storage, with no significant change in lipid bound sialic acid concentration. In a preferred embodiment, the paper strip is impregnated with an agent which improves the sample's stability, e.g., a pH 7-8 $NaHCO_3$ solution, or a 1% sodium azide solution (w/v), or a 0.01-1.0% benzamidine hydrochloride solution (w/v) or a 0.001-0.01% phenylmethylsulfonyl fluoride solution (w/v). In addition, standard known samples may be prepared by any of the previously mentioned methods.

The initial step of the method of the present invention is to dilute a predetermined volume of a blood plasma or serum sample with distilled water. The volume dilution is about two–five times e.g., about four times the volume of initial plasma sample. Thus, if the initial plasma or serum sample is 50 $\mu$l in a small tube or container, the amount of distilled water added may be about 150 $\mu$l to produce about 200 $\mu$l of diluted sample, i.e., about four times the volume of the initial sample. If the initial sample has been dried onto paper or another suitable support the volume dilution is based on the volume of the liquid sample before it was placed on the paper strip or other suitable support. Thus, if a 50 $\mu$l sample of blood plasma is dried onto the support, the amount of distilled water added again may be 150 $\mu$l.

The diluted sample is mixed, e.g., by vortexing, for a suitable time to obtain a substantially homogeneous sample, e.g., at least 5 seconds. The mixed, diluted sample is then cooled to about 0°–5° C., e.g., by placing the tube or container in which the sample is held in crushed ice.

A mixture of a chlorinated lower alkyl hydrocarbon and a lower alkyl alcohol in which the volume ratio of chlorinated hydrocarbon to alcohol is about 2 to 1 is then added to the cooled sample. The volume of the chlorinated hydrocarbon and alcohol mixture added is about sixty times the original, i.e. predetermined, volume of the plasma sample and its temperature is about 0°–5° C. Thus, if the original sample volume is 50 $\mu$l, the volume of mixture added is about 3 ml. Suitable chlorinated hydrocarbons include chloroform, methylene chloride, ethylene chloride, propylene chloride and carbon tetrachloride, chloroform being presently preferred. The lower alkyl alcohol may be methanol, ethanol, propanol, n-butanol, isopropanol, isobutanol or isoamyl alcohol. However, as Table II shows, the greater the number of carbon atoms in the alcohol, the less effective the mixture is in terms of lipid bound sialic acid extraction as opposed to total sialic acid extraction. Stated differently, the greater the number of carbon atoms in the alcohol, the greater the amount of sialic acid which is not lipid bound which is precipitated. Therefore, the preferred alcohol is methanol since the other alcohols extract higher amounts of total sialic acid, i.e., lipid bound plus unbound sialic acid and other contaminants, and therefore reduce the diagnostic value of the test.

TABLE II

EFFECT OF VARYING LOWER ALKYL ALCOHOL IN 2:1 CHLOROFORM:ALCOHOL MIXTURE UPON AMOUNT OF TOTAL SIALIC ACID EXTRACTED MEASURED IN MGS %

| TYPE OF SAMPLE | $CHCl_3$: METHANOL | $CHCl_3$: ETHANOL | $CHCl_3$: PROPANOL | $CHCl_3$: n-BUTANOL | $CHCl_3$: ISOPROPANOL | $CHCl_3$: ISOBUTANOL | $CHCl_3$: ISOAMYL ALCOHOL |
|---|---|---|---|---|---|---|---|
| NORMAL | 17.8 | 28.0 | 35.0 | 51.3 | 55.7 | 62.0 | 61.0 |
| NORMAL | 19.8 | 33.7 | 41.6 | 51.4 | 62.8 | 60.0 | 60.4 |
| CANCER | 25.7 | 56.3 | 62.3 | 61.6 | 65.0 | 64.0 | 61.9 |
| CANCER | 40.2 | 71.4 | 88.7 | 89.0 | 100.2 | 95.1 | 99.0 |

The resulting admixture is then mixed for a suitable period of time to dissolve matter present in the sample in the chlorinated hydrocarbon/alcohol mixture, preferably by gentle interrupted vortexing for at least 20 seconds and more preferably by vortexing gently at least 10 seconds with three interruptions, allowing the mixture to stand for at least 20 seconds followed by vortexing gently at least 10 additional seconds with three interruptions. Inadequate or overly vigorous vortexing may affect the assay results. The admixture is then diluted with deionized distilled water, pH 5-6, at a temperature from about 0°–5° C., the volume added being about ten times the predetermined volume of the blood plasma or serum sample. Thus, if the original plasma sample were 50 $\mu$l and the amount of chlorinated hydrocarbon:alcohol mixture were 3 ml, the amount of water added would be about 0.5 ml.

The diluted admixture is then treated, first by mixing the diluted admixture for a suitable period of time, e.g., by gentle interrupted vortexing for at least 20 seconds, and more preferably the vortexing being for at least 10 seconds with three interruptions, allowing the mixture to stand for at least 20 seconds followed by at least 10 additional seconds with three interruptions. Inadequate or overly vigorous vortexing at this step also may affect the assay results. The mixture is then centrifuged for at least about two minutes at above 2000 rpm (750 xg) to yield a substantially clear upper phase.

A predetermined volume of the upper phase is then separately recovered from the substantially clear upper phase so formed, preferably by removing the upper phase from the lower phase and discarding the latter. The predetermined volume so recovered will depend upon the volume of the original plasma sample. Thus, if the original, i.e. predetermined, plasma volume is about 50 μl, the volume of upper phase separately recovered will be about 1 ml. The predetermined volume of the upper phase which is separately recovered will depend upon the convenience of removing a large volume of the upper phase without disturbing the interface or other material in the tube.

To the predetermined volume of the upper phase there is added an amount of a mixture of a protein-precipitating agent and an adsorbing material, the amount of mixture added being effective to cause precipitation of the lipid bound sialic acid and to adsorb the precipitated lipid bound sialic acid. Suitable protein-precipitating agents include phosphotungstic acid, trichloroacetic acid, ammonium sulfate (e.g., saturated pH 4.0-6.0 buffered solution) or mixtures thereof (e.g., 90% phosphotungstic acid; 10% trichloroacetic acid). Suitable adsorbing materials include siliceous materials such as silica and silica gel and aluminum oxide, with or without additional binder materials. In the mixture of protein-precipitating agent and adsorbing material the relative amount by dry weight of the former to the latter is about 3:1. The presently preferred mixture contains about 75% phosphotungstic acid and 25% silica gel (on a dry weight basis) and the amount added is about 60-80 mgs per ml of upper phase. The presently preferred silica gels are available from MCB Manufacturing Chemists, Inc., Grades 950 and 62 (60-200 mesh). Another preferred mixture contains about 25% $Al_2O_3$ (Florisil ®—30-60 mesh) in place of silica gel.

The resulting admixture is then mixed, e.g., by vortexing briefly (at least 3 seconds), and the resulting precipitate is recovered, e.g., by centrifugation for at least 3 minutes at a speed above about 2000 rpm and discarding the supernatant. The precipitate is then suspended in a suitable volume of distilled water for convenient handling, e.g., about 1 ml. and the amount of lipid bound sialic acid present in the suspended precipitate and thereby the amount present in the blood plasma sample is determined. More specifically, the amount of lipid bound sialic acid is determined by adding to the suspended precipitate a suitable volume, e.g., 1 ml, of resorcinol reagent, mixing, boiling for 15 minutes, cooling for at least about 10 minutes in an ice bath, centrifuging for at least 2 minutes at about 2000 rpm, adding about twice said suitable volume, e.g., 2 mls, of a mixture of butyl acetate and n-butanol (85:15 v/v), mixing, centrifuging for at least 5 minutes at above about 2000 rpm, separating the organic layer, reading at 580 nm the extracted blue color present in the organic layer, determining the amount of lipid bound sialic acid using standard curves developed from a known sample of n-acetyl neuraminic acid (NANA) under the same conditions and applying the formula:

$$\text{LSA (mg/100 ml plasma)} = (x \cdot 10^5 \, \mu l)/(y \cdot z \, \mu l \cdot 1000)$$

where $x = \gamma$ NANA read from standard curve, $y =$ the predetermined volume of the upper phase recovered ÷ total volume of the entire upper phase and $z =$ the predetermined sample volume, e.g. 50 μl, of the blood plasma or serum sample.

The various steps of sample handling and manipulation in the various embodiments of this invention, e.g. addition of reagents, cooling, mixing, recovering aliquot volumes, centrifuging, etc., may be automated, e.g. with a suitably programmed robotic device(s) appropriately interfaced with suitable equipment for effecting the manipulations, e.g. syringes, delivery tubes, centrifuge, vortexer or other mixing apparatus, etc. Materials may be appropriately cooled by using jacketed delivery tubes or receptacles in which the jacketed portion is supplied with a coolant fluid maintained at a suitable reduced temperature. Similarly the absorbance of light due to the presence of sialic acid may be detected automatically with an appropriately programmed detection apparatus, e.g. a spectrophotomer, suitably interfaced with the robotic device(s). Likewise, the amount of lipid bound sialic acid may be calculated directly from the absorbance so detected using a suitably programmed computer, e.g. microcomputer, appropriately interfaced with the detection device. By automating the method as described above, a reduction in cost per assay and an improvement in the coefficient of variation for the assay may be achieved.

This invention also provides a method of diagnosing cancer in a human subject which comprises determining the amount of lipid bound sialic acid in a sample of the subject's blood plasma or serum according to the method described herein and comparing the amount so determined with values obtained for subjects known to have cancer, or alternatively comparing the amount so determined with values obtained over a period of time for the same subject.

Furthermore, this invention provides a cancer diagnostic kit comprising suitable supports, e.g., paper strips or circles for the sample to be tested, preferably impregnated with a stabilizing agent; suitable supports, e.g., paper strips or circles onto which known amounts of reference samples and n-acetyl neuraminic acid standards have been dried; mixtures of chlorinated hydrocarbon and lower alkyl alcohol (2:1 v/v); mixture of precipitating agent and adsorbing material; resorcinol reagent; mixture of butylacetate-n-butanol and n-butanol (85:15 v/v); deionized distilled water and pipette tips for the sample.

Finally, this invention provides an improvement in methods for determining the amount of lipid bound sialic acid in a sample of human blood plasma or serum involving extraction from the sample, e.g., using a mixture of chlorinated hydrocarbon and lower alkyl alcohol, followed by precipitation of the lipid bound sialic acid using a protein precipitating agent. This improvement involves the use of an adsorbing material in admixture with the protein precipitating agent, the amount thereof being effective to cause precipitation of lipid bound sialic acid and adsorption of the precipitated lipid bound sialic acid on the adsorbing material.

It is contemplated that use of this improvement will enable the invention to provide advantages relative to previous methods over a wide range of variation in method parameters and that the more detailed method described herein will prove to be only a preferred embodiment of a more general method.

The examples which follow are set forth to aid in an understanding of the invention but are not intended to, and should not be construed to, limit in any way the invention as set forth in the claims which follow thereafter.

EXAMPLES

Example 1

Plasma Collection

Whole blood is collected in a vacutainer (purple cap) with liquid EDTA (Venoject lavender stopper tubes containing 15% EDTA) or microtainer with EDTA coated beads. After mixing by inversion several times, the tubes are centrifuged at 2200 rpm for 10 minutes in a bench-type clinical centrifuge (IEC HN-S-II centrifuge, Damon/International Equipment Co. with an IEC #958 6-position rotor). Aliquots of the separated plasma are either stored at −20° C. for several months before analysis or analyzed fresh.

Example 2

Determination of Lipid Bound Sialic Acid in a 50 μL Plasma Sample

50 μl of a sample of plasma prepared in accordance with Example 1 is placed in a suitable tube or container. 150 μl of distilled water is added, the resulting mixture is vortexed for 5 seconds and the container is then transferred the crushed ice. 3 ml of 2:1 chloroform:methanol (4°–5° C.) is then added. Chloroform, methanol and other solvents were obtained in Analytical Reagent (AR) grade from Mallinckrodt Inc. The mixture is vortexed (Vortex-Genie®, Scientific Industries, Inc.) for 10 seconds with three interruptions, and then after 40 seconds vortexed again for an additional 10 seconds with three interruptions (for a total vortexing time of 20 seconds). 0.5 ml of deionized distilled water, pH 5–6, (4°–5° C.) is then added and the sample vortexed for 10 seconds with three interruptions, and after 40 seconds vortexed for an additional 10 seconds with three interruptions. The sample is then centrifuged for 5 minutes at 2500 rpm. 1 ml of the resulting upper phase is transferred to a separate tube and 60°80 mg of a mixture of 75% phosphotungstic acid (AR grade, Sigma) and 25% silica gel (60F254 MCB Manufacturing Chemists, Inc.) is added in the form of a dried powder. The resulting sample is then vortexed briefly and centrifuged for 5 minutes at a speed above 2000 rpm. The resulting supernatant is removed and the precipitate is then vortexed briefly and 1 ml of distilled water is added and brief vortexing again performed. 1 ml of resorcinol reagent at 0°–4° C. is then added. The sample is vortexed and then placed in boiling water for 15 minutes. Immediately after boiling the sample is placed in an ice and water bath for 5 minutes. Thereafter the cold tube is centrifuged for 1 to 2 minutes at a speed above 2000 rpm. 2 ml of butylacetate and butanol mixture (85:15 v/v) is added, and the simple vortexed and centrifuged for 5 minutes at a speed above 2000 rpm. The extracted blue color is then read at 580 nm (Model 34 spectrophotometer, Beckman Instruments, Inc.) and the amount of lipid bound sialic acid determined by use of a standard curve developed from a standard sample of n-acetyl neuraminic acid using the formula:

$$\text{LSA (mg/100 ml plasma)} = (x \cdot 10^5 \mu l)/(y \cdot 50 \mu l \cdot 1000)$$

where x=NANA read from standard curve and y=1 ml of the upper phase recovered÷total volume of entire upper phase.

Example 3

Use of Paper Strip

Plasma collection paper (Schleicher & Schuell #903) in a strip 1.0×0.5 cm is used. 50 μl of plasma is loaded onto the strip with a pipetter and a tip. The strip is dried in the air for 5 minutes and cut into small pieces with scissors at the time it is placed into the analysis tube. The tube is then covered and kept at room temperature until further processing. To the tube with the cut-up strips and 150 μl of distilled water and then proceed with the procedure as described in Example 2.

Example 4

Preparation of Impregnated Paper

A 0.1% solution of sodium azide (Fisher, 316 MA, purified) in water is prepared. 50 μl of this solution is applied to a 1.5×1.0 cm strip of filter paper (Schleicher & Schuell #903). The strip is dried under a stream of hot air. To this strip 50 μl of plasma is applied and the plasma dried prior to analysis. The strip may be stored for a substantial period of time at room temperature prior to analysis.

Example 5

Resorcinol Reagent

1. Stock Resorcinol solution (2%) In a 100 ml volumetric flask weigh out 2 grams of resorcinol (SIGMA #R-1000). Fill up to the mark with distilled water. Keep the solution refrigerated in a dark bottle.
2. Cupric sulfate 0.1M ($CuSO_4.5H_2O$ MALLINCKRODT #4844) In a 100 ml volumetric flask weigh out 2.497 gm of $CuSO_4.5H_2O$. Fill up to the mark with distilled water.
3. HCl conc. FISHER Co. #A-144

Preparation of Resorcinol Reagent

In a 100 ml volumetric flask add:
(a) 10 ml of 2% stock resorcinol solution
(b) 0.25 ml of 0.1M $CuSO_4$ (Mix)
(c) 9.75 ml distilled water (Mix)
(d) fill up to the mark with HCl.
Mix, transfer to a dark container and store at 0°–5° C.

Example 6

Preparation of Reference Sample

A paper strip (Schleicher & Schuell #903) is used for the absorption of 50 μl of a sample of known LSA concentration. The strip (1.0×0.5 cm) is dried in the air for 5 minutes and then cut into small pieces at the time it is placed into the analysis tube. The tube is covered until the time for analysis at which point the procedure described in Example 2 is followed.

Example 7

Standard Nana Curve Construction

N-acetyl neuraminic acid (98% SIGMA) is used for the standard NANA solution at a concentration of 1 mg/ml. The same types of filter paper and procedures are used to construct the standard curve except that instead of using 50 μl of plasma 5, 10 and 15 μl of the standard NANA solution is employed. The same procedures are employed as described in Example 2 for determining LSA content and a linear standard curve constructed which can be used as a reference for comparison with the values determined using the method of present invention.

Example 8

Table III sets forth a comparison of the results obtained when lipid bound sialic acid values were determined for a normal range sample and a low range sample using the procedure described in U.S. Pat. No. 4,342,567 and the procedure of the present invention. As Table III clearly indicates the standard deviation observed with the method of this invention is significantly better than that obtained with the prior method.

TABLE III

COMPARISON OF LSA VALUES BY THE PREVIOUS PROCEDURE[1] AND THE PROCEDURE OF THIS INVENTION ON A NORMAL RANGE SAMPLE AND A LOW RANGE SAMPLE

| | PLASMA LSA mgs % IN NORMAL RANGE | | | PLASMA LSA mgs % IN LOW RANGE | |
|---|---|---|---|---|---|
| ALIQUOT | PREVIOUS PROCEDURE[1] | NEW PROCEDURE (PTA ETC.) | ALIQUOT | PREVIOUS PROCEDURE[1] | NEW PROCEDURE |
| 1 | 15.4 | 14.6 | 1 | 2.9 | 3.3 |
| 2 | 15.4 | 15.7 | 2 | 3.9 | 3.5 |
| 3 | 14.3 | 14.0 | 3 | 1.6 | 3.5 |
| 4 | 12.6 | 15.1 | 4 | 1.2 | 2.4 |
| 5 | 14.0 | 14.9 | 5 | 4.0 | 2.9 |
| 6 | 14.3 | 14.9 | 6 | 1.1 | 2.3 |
| 7 | 14.0 | 14.6 | 7 | 3.4 | 3.8 |
| 8 | 13.4 | 14.9 | 8 | 2.0 | 2.8 |
| 9 | 15.4 | 16.3 | 9 | 3.1 | 2.6 |
| 10 | 14.0 | 14.6 | 10 | 2.5 | 2.4 |
| Average ± s.d. | 14.3 ± 0.9 | 15.0 ± 0.6 | | 2.6 ± 0.9 | 3.0 ± 0.4 |
| % s.d. | 6.3% | 4.0% | | 34.6% | 13.3% |

[1] U.S. Pat. No. 4,342,567

Example 9

Lipid-Associated Sialic Acid Concentration (LASA) in Chronic Lymphocytic Leukemia (CLL).

LASA has previously been found to correlate with the presence of tumor in patients with cancer (Katopodis N., et al., Cancer Research, 1982). The LASA value was determined by the method of Example 2 in 34 patients with CLL, and in 100 control patients without malignancy. All patients were staged by the Rai clinical staging criteria. The results are tabulated below:

| | No. of Patients | Plasma LASA Concentration | |
|---|---|---|---|
| | | Mean + S.D. (mg/dl) | Range (mg/dl) |
| Controls | 100 | 18.1 ± 3.1 | 9–21 |
| Stage 0 | 11 | 18.8 ± 3.4 | 14–27 |
| Stage I | 5 | 21.8 ± 3.2 | 17–28 |
| Stage II | 10 | 23.0 ± 5.4 | 17–34 |
| Stage III/IV | 8 | 26.6 ± 7.8 | 20–45 |

In 12 patients, serial determinations were made over a 6-month period. In 9 of these patients LASA values and clinical status were unchanged. In the 3 patients with an increase in LASA values, there was also progression of disease activity. In 2 patients, the increase in LASA preceded clinically apparent progression of disease by 4 and 6 weeks.

These findings suggest that LASA determinations correlate with clinically active disease and may be of value in monitoring the course of patients with CLL.

Example 10

CA-125, CEA, and LSA in the Monitoring of Ovarian Cancer Patients

Serial serum specimens from five ovarian carcinoma patients were evaluated by three tumor marker assays: CEA, CA-125, and Lipid-associated Sialic Acid (LSA). CEA and CA-125 antigen were assayed using reagents commercially available from Abbott Laboratories, No. Chicago, Ill. and Centocor, Malvern Pa., respectively. LSA was assayed by the method of Example 2. Specimens secured at time of diagnosis from all five patients showed elevated levels of both LSA and CA-125. None had elevated CEA values. In all five patients LSA and CA-125 levels fell to normal following surgery and chemotherapy. They remained in the normal range in two patients who continued free of disease during a two-year follow-up period. In the remaining three patients both CA-125 and LSA levels increased as disease progressed or recurred. In one patient the LSA level increased significantly about one month prior to clinical evidence of recurrence while CA-125 increased at the time of recurrence.

In this limited sample LSA and CA-125 assays, but not CEA, appeared to be useful in the monitoring of ovarian cancer patients. The value of their combined use appears particularly promising.

What is claimed is:
1. A method for extracting lipid bound sialic acid from human blood plasma or serum and determining the amount of lipid bound sialic acid in a sample of human blood plasma or serum which comprises the following steps:
  (a) diluting a predetermined volume of a blood plasma or serum sample with distilled water to a volume about four times that of the predetermined volume of the sample;
  (b) mixing the diluted sample for a suitable period of time to obtain a substantially homogenous sample;
  (c) cooling the mixed, diluted sample to about 0°–5° C.;
  (d) adding to the cooled sample a mixture of a chlorinated lower alkyl hydrocarbon and a lower alkyl alcohol, the volume of the mixture added being about sixty times the predetermined volume of the blood plasma or serum sample, and the volume ratio of chlorinated hydrocarbon to alcohol in the mixture being about 2:1 and its temperature about 0°–5° C.;
(e) mixing the resulting admixture for a suitable period of time to dissolve lipid-bound or unbound sialic acid containing matter present in the sample in the chlorinated hydrocarbon/alcohol mixture;
(f) diluting the admixture with deionized distilled water at a temperature from about 0°–5° C., the volume of water added being about ten times the predetermined volume of the blood plasma or serum sample;
(g) mixing the diluted admixture for a suitable period of time to obtain a substantially homogeneous admixture and centrifuging the mixture to form a substantially clear upper phase;
(h) separately recovering from the clear upper phase so formed a predetermined volume of the upper phase;
(i) adding to the predetermined volume of the upper phase an amount of a mixture of a protein-precipitating agent and an adsorbing material, the amount of mixture being effective to cause precipitation of the lipid bound sialic acid and to absorb the precipitated lipid bound sialic acid;
(j) mixing the resulting admixture;
(k) separately recovering the resulting absorbed precipitate;
(l) suspending the precipitate in a volume of distilled water; and
(m) determining the amount of lipid bound sialic acid present in the suspended precipitate and thereby the amount present in the blood plasma or serum sample.

2. A method according to claim 1, wherein in step (a) the predetermined volume is about 50 μl and is diluted with about 150 μl of distilled water.

3. A method according to claim 1, wherein in step (b) the mixing comprises vortexing for at least 5 seconds.

4. A method according to claim 2, wherein in step (d) the volume of the added mixture is about 3 ml.

5. A method according to claim 1, wherein in step (d) the lowr alkyl alcohol is methanol, ethanol, propanol, n-butanol, isopropanol, isobutanol or isoamyl alcohol.

6. A method according to claim 5, wherein in step (9) the lower alkyl alcohol is methanol.

7. A method according to claim 1, wherein in step (d) the chlorinated lower alkyl hydrocarbon is chloroform.

8. A method according to claim 1, wherein in step (e) the mixing comprises gentle interrupted vortexing for at least 20 seconds.

9. A method according to claim 2, wherein in step (f) the volume of water added is about 0.5 ml.

10. A method according to claim 1, wherein in step (g) the treating comprises gentle interrupted vortexing for at least 20 seconds followed by centrifuging at above about 2,000 rpm for at least 5 minutes.

11. A method according to claim 1, wherein in step (h) the separately recovering comprises removing the upper phase from the lower phase.

12. A method according to claim 2, wherein in step (h) the predetermined amount of the upper phase is about 1 ml.

13. A method according to claim 1, wherein in step (i) the protein-precipitating agent is phosphotungstic acid, trichloroacetic acid, ammonium sulfate or a mixture thereof.

14. A method according to claim 1, wherein in step (i) the adsorbing material comprises a siliceous material.

15. A method according to claim 14, wherein the siliceous material is silica or silica gel.

16. A method according to claim 1, wherein in step (i) the relative amount by dry weight of proteinprecipitating agent to adsorbing material in the mixture is about 3:1.

17. A method according to claim 16, wherein the mixture comprises about 75% phosphotungstic acid and about 25% silica gel on a dry weight basis.

18. A method according to claim 12, wherein in step (i) the mixture comprises about 75% phosphotungstic acid and about 25% silica gel on a dry weight basis and the amount of mixture comprises about 60–80 mgs.

19. A method according to claim 1, wherein in step (j) the mixing comprises vortexing for at least 3 seconds.

20. A method according to claim 1, wherein in step (k) the separately recovering comprises centrifuging for at least 3 minutes at a speed above about 2000 rpm.

21. A method according to claim 12, wherein in step (l) the volume is about 1 ml.

22. A method according to claim 1, wherein in step (m) the amount of lipid bound sialic acid is determined by adding to the suspended precipitate a volume of resorcinol reagent, mixing, boiling for 15 minutes, cooling for about 10 minutes in an ice bath, centrifuging for at least 2 minutes at above about 2000 rpm, adding a mixture of butylacetate and n-butanol (85:15 v/v) in a volume about twice said volume of resorcinal reagent mixing, centrifuging for about 5 minutes at above about 2000 rpm, separating the organic layer, reading at 580 nm the extracted blue color present in the organic layer, determining the amount of lipid bound sialic acid by comparing the reading obtained at 580 nm to a standard curve developed from a known sample of n-acetyl neuraminic acid (NANA) under the same conditions and applying the formula:

$$\text{LSA (mg/100 ml plasma)} = (x \cdot 10^5 \, \mu l)/(y \cdot z \, \mu l \cdot 1000)$$

where x=NANA read from standard curve, y=the volume of the upper phase recovered÷total volume of entire upper phase and z=the predetermined volume of the blood plasma or serum sample.

23. A method according to claim 22, wherein the volume of resorcinol reagent is about 1 ml.

24. A method according to claim 1, wherein in step (a) the blood plasma or serum sample to be tested is dried onto a support means.

25. A method according to claim 24, wherein the support means is a filter paper strip or circle.

26. A method according to claim 24, wherein the support means has previously been impregnated with a stabilizing agent.

27. A method according to claim 26, wherein the stabilizing agent is a pH 7–8 NaHCO$_3$ solution, or a 1% (w/v) sodium azide solution, or a 0.01–1.0% (w/v) benzamidine hydrochloride solution or a 0.001–0.01% (w/v) phenylmethyl sulfonyl fluoride solution.

28. A method of diagnosing cancer in a human subject which comprises determining the amount of lipid bound sialic acid in a sample of the subject's blood plasma or serum according to the method of claim 1 and comparing the amount so determined with values obtained for subjects known to have cancer.

29. A method of diagnosing cancer in a human subject which comprises determining at regular time intervals the amount of lipid bound sialic acid in a sample of the subject's blood plasma or serum according to the method of claim 1 and comparing the amounts so determined with amounts previously obtained for the subject.

30. A cancer diagnostic kit comprising sample support means on which the test sample is to be placed; sample support means onto which known amounts of reference sample and n-acetyl neuraminic acid standards have been dried; a container of a mixture of chlorinated lower alkyl hydrocarbon and lower alkyl alcohol (2:1 v/v); a container of a mixture of protein precipitating agent and adsorbing material; a container of resorcinol reagent; a container of a mixture of butyl acetate and n-butanol (85:15 v/v); a container of deionized distilled water and pipette tips for the sample.

31. A cancer diagnostic kit comprising paper strips or circles for the sample to be tested; paper strips or circles onto which known amounts of reference sample and n-acetyl neuraminic acid standards have been dried; a container of a mixture of chloroform and lower alkyl alcohol (2:1 v/v); a container of a mixture of protein precipitating agent and adsorbing material; a container of resorcinol reagent; a container of a mixture of butyl acetate and n-butanol (85:15 v/v); a container of deionized distilled water and pipette tips for the sample.

32. A cancer diagnostic kit according to claim 31, wherein the paper strips or circles are impregnated with a stabilizing agent.

33. A cancer diagnostic kit according to claim 31, wherein the lower alkyl alcohol is methanol, the precipitating agent is phosphotungstic acid, the adsorbing material is silica gel and the mixture thereof contains 75% phosphotungstic acid and 25% silica gel on a dry weight basis.

34. In a method for determining the amount of lipid bound sialic acid in a sample of human blood plasma or serum involving extraction of the lipid bound sialic acid from the sample and precipitation of the lipid bound sialic acid using a protein precipitating agent the improvement comprising using an adsorbing material in admixture with the protein precipitating agent, the amount of admixture being effective to cause precipitation of the lipid bound sialic acid and adsorption of the precipitated lipid bound sialic acid on the adsorbing material.

35. A method according to claim 1, wherein in step (d) the chlorinated lower alkyl hydrocarbon is chloroform, methylene chloride, ethylene chloride, propylene chloride or carbon tetrachloride.

* * * * *